United States Patent [19]
Mayzels et al.

[11] Patent Number: 5,339,803
[45] Date of Patent: Aug. 23, 1994

[54] SELF-HINGING DISPOSABLE RETRACTOR INSTRUMENT FOR ENDOSCOPIC SURGERY

[76] Inventors: Ilya Mayzels, 2451 Coldwater Cyn. Dr., Beverly Hills, Calif. 90210; Joseph Shvager, 10847 Wystone Ave., Northridge, Calif. 91326

[21] Appl. No.: 46,666

[22] Filed: Apr. 13, 1993

[51] Int. Cl.⁵ ............................................. A61B 17/02
[52] U.S. Cl. ..................................... 128/20; 606/198; 604/105
[58] Field of Search ........................ 128/20, 17, 18, 3; 606/191, 198; 604/104–109; 294/19.1, 19.2, 19.3, 22, 23

[56] References Cited

U.S. PATENT DOCUMENTS

| | | | |
|---|---|---|---|
| 832,201 | 10/1906 | Kistler | 606/198 X |
| 2,320,611 | 6/1943 | Kandle | 273/162. E X |
| 3,857,395 | 12/1974 | Johnson et al. | 606/198 X |
| 4,236,742 | 12/1980 | Florence | 294/19.2 X |
| 4,592,341 | 6/1986 | Omagari et al. | 604/105 X |
| 5,112,310 | 5/1992 | Grobe | 604/105 X |
| 5,178,133 | 1/1993 | Pena | 604/105 X |
| 5,195,505 | 3/1993 | Josefsen | 128/20 |

Primary Examiner—Richard J. Apley
Assistant Examiner—Donna L. Maraglio
Attorney, Agent, or Firm—Frederick Gotha

[57] ABSTRACT

An endoscopic surgical retractor instrument is presented which has a laterally collapsible and expandable self-hinging truss support platform carried by a sleeve and extension member. The sleeve is slideably carried by the extension member and consists of first and second arcuate sections which are radially and oppositely carried by the extension member and captively contained thereon by the inner surface of a housing cavity. The housing has a distal barrier adjacent its distal end which defines a limit to the distal axial displacement of the sleeve relative to the housing. Upon engagement of the distal barrier by the sleeve, the continued distal axial displacement of the extension member will cause expander struts in the truss support platform to expand the platform's outer struts laterally thereby opening the truss. Upon retraction of the expansion member in the housing, the outer struts collapse laterally and continued axial proximate displacement of the extension member will cause the expander struts to collapse laterally and close the truss.

17 Claims, 4 Drawing Sheets

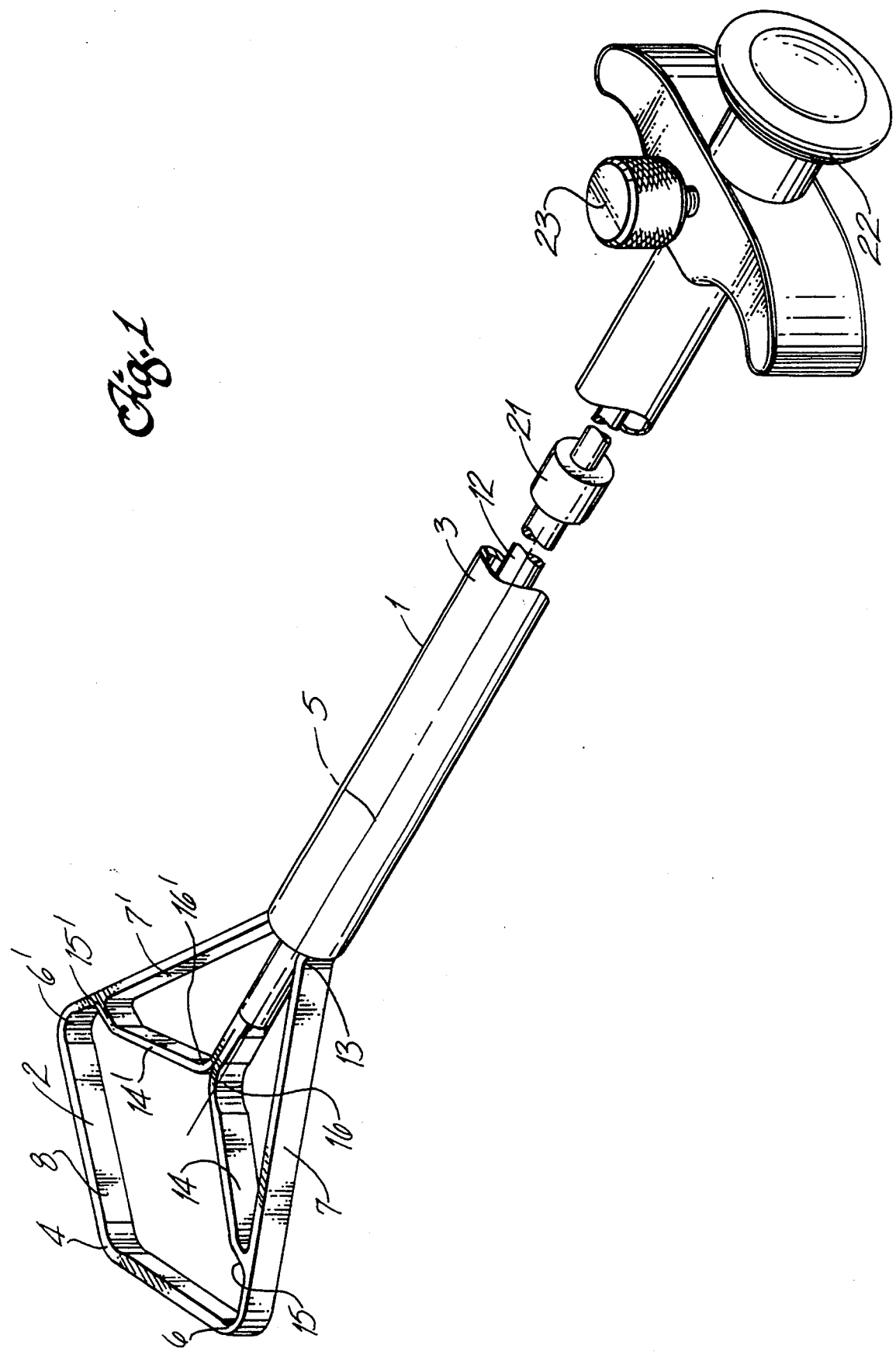

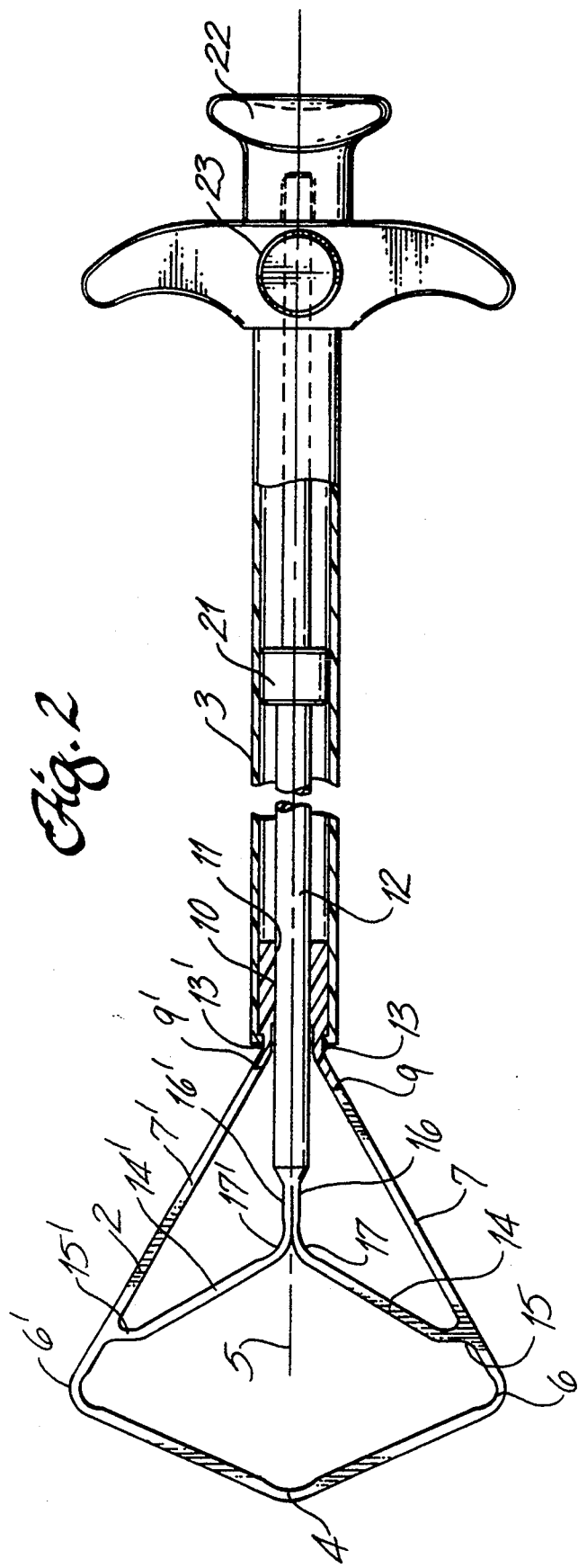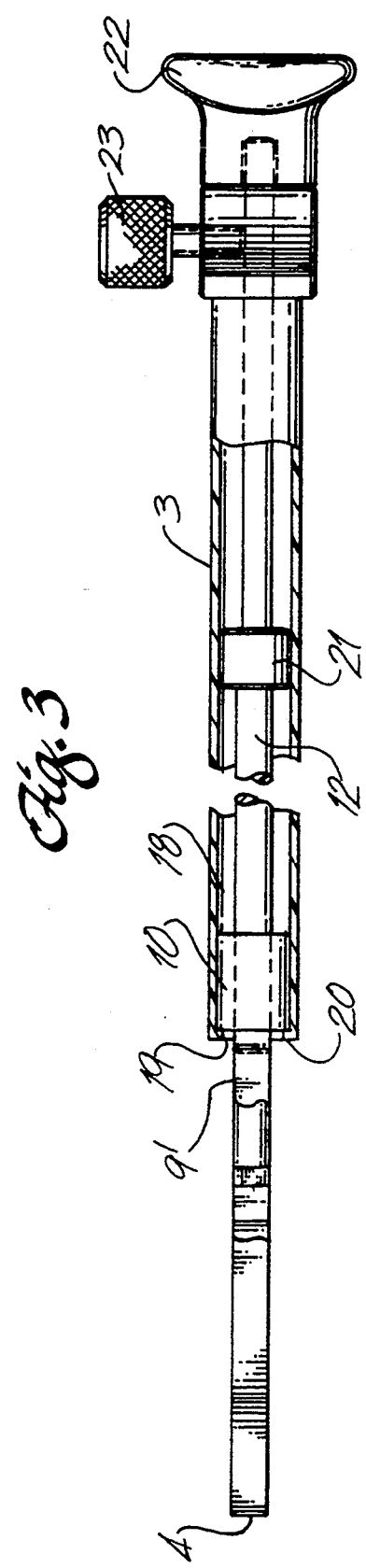

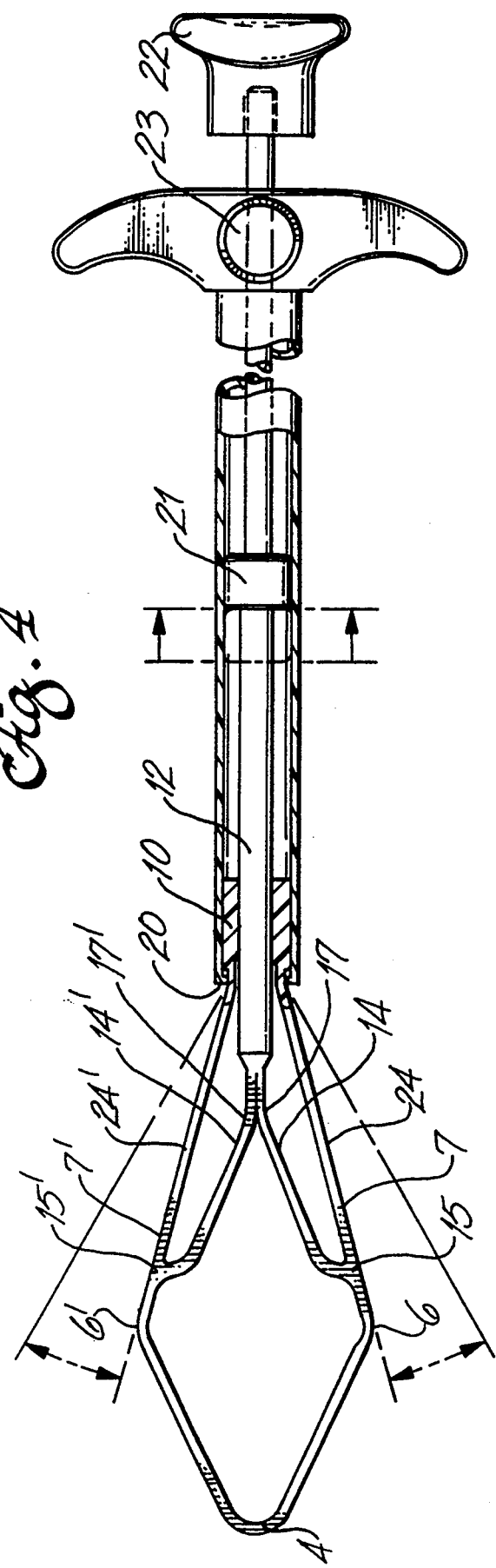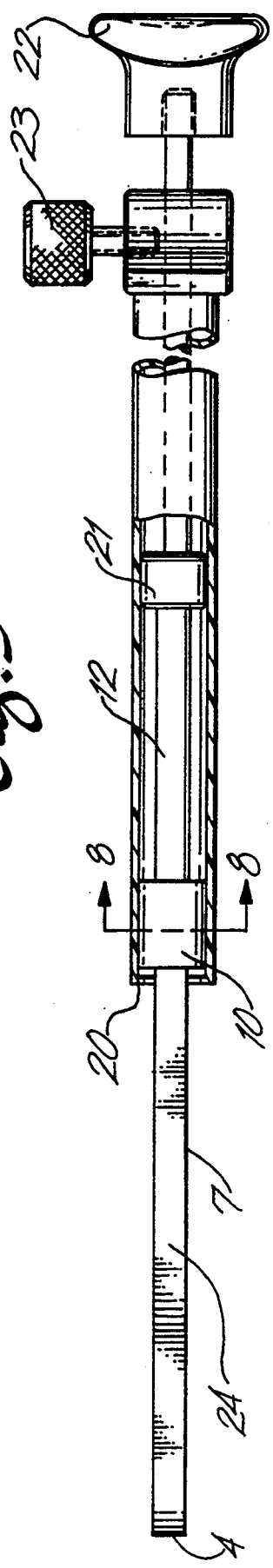

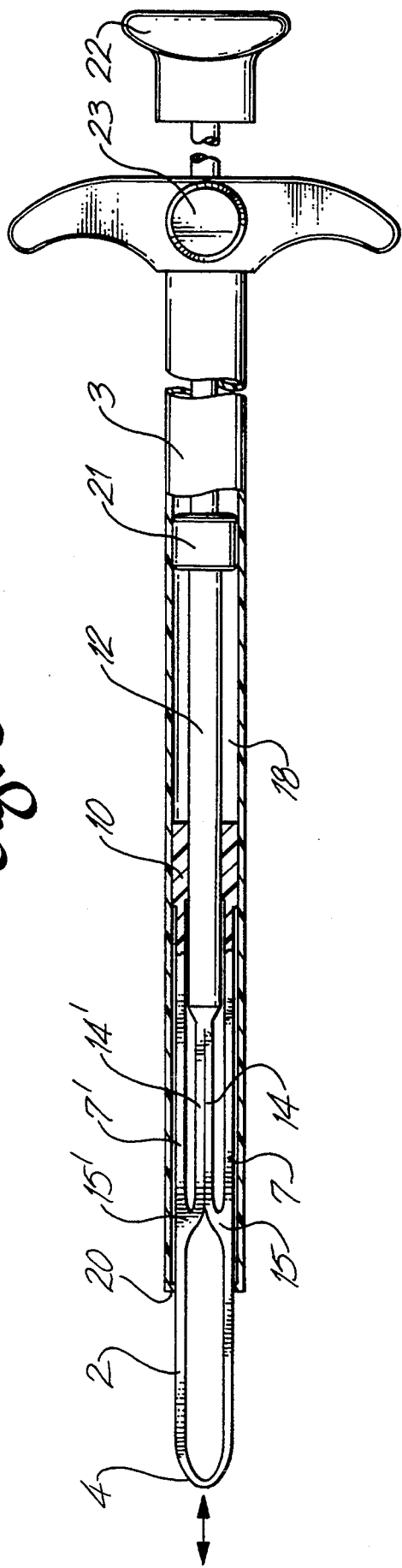
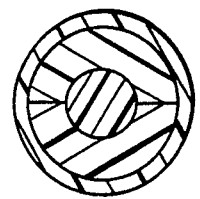
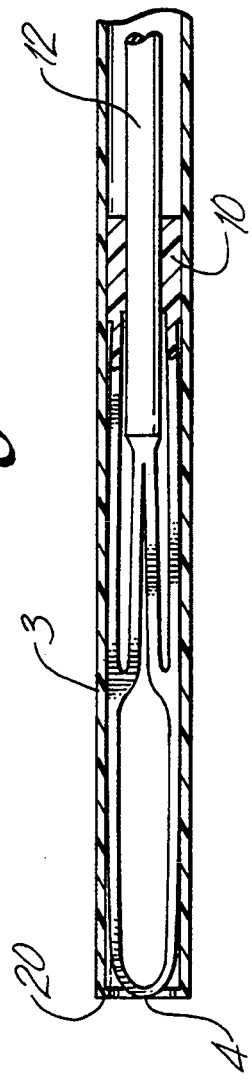

SELF-HINGING DISPOSABLE RETRACTOR INSTRUMENT FOR ENDOSCOPIC SURGERY

FIELD OF THE INVENTION

This invention relates to a disposable surgical endoscopic retractor instrument used to retain or hold back internal internal organs in the operative region during minimimally invasive surgery.

BACKGROUND OF THE INVENTION

Minimally invasive surgery has brought about significant economies in hospital costs and patient productivity largely because of reduced hospital confinement and patient rehabilitation time. The instruments used to perform such surgery however, still contribute substantially to the expense of the surgery because of the miniturization required of such instruments, sterilization requirements, and material costs. Retractor instruments of the prior art for minimally invasive surgery are usually of a spring wire construction or made of a multi-joint lever system composed of a plurality of metallic support arms which are pivotally interconnected to form a truss support platform. The manufacturing and material costs of metallic retractors is substantially more expensive for metallic retractors than plastic retractors and therefore the use of metallic retractors as disposable retractors is economically restrictive. A disposable retractor made of a plastic material molded such that the retractor has a continuous truss surface with self-hinging joints integrally formed with the surfaces presents an instrument which is readily sterilizable and inexpensive to manufacture; non-disposable retractors, on the other hand, to be reusable, require sterilization after each use. Metallic multi-joint lever system-type retractors having support arms pivotally hinged to each other are less readily sterilized because of the tendency of small particles to adhere to pivoting joints. These retractors are prohibitively expensive for disposable use and present increased surgical risk without cost reduction due to the sterilization process required after each use.

SUMMARY OF THE INVENTION

There is, therefore, provided according to the present invention, an endoscopic, self-hinged, plastic disposable retractor instrument having a self-hinging truss which is integrally formed at the distal tip of an extension member and of one piece construction; the self-hinging truss is laterally collapsable to permit insertion of the truss into a housing for tranportation through a trocar communicating with the operative region. The truss is made of a plastic material and of continuous construction and because its interconnecting members are self-hinged, the instrument has the advantage of being more readily sterilized than retractors of the type having a pinned joint truss construction with articulating arms. The extension member and truss are manufactured in one piece through plastic injection molding which greatly reduces the cost of manufacture and thus permits the instrument to be disposable after each use.

The present invention is directed to an endoscopic disposable retractor instrument made of a plastic material and comprised of a laterally collapsable self-hinging truss. The self-hinging truss is integrally formed with an extension member which has a longitudinal axis and is slideably mounted within an axially extending cavity contained within a housing. The extension member is mounted so as to permit axial movement of the extension member relative to the housing. A cylindrically shaped cavity is contained within the housing and extends longitudinally through the housing so that the extension member may, by external force applied at the proximate end of the extension member, be axially displaced relative to the housing. Because of the lateral collapsability of the truss, upon insertion or retraction of the truss into the cavity of the housing at its proximate or distal end, the cavity wall will induce collapse of the truss. The truss has a pair of laterally and oppositely spaced outer struts which are integrally connected at their proximate ends to a sleeve so as to form a pair of self-hinging joints which allow the outer struts to be laterally collapsable. The sleeve is slideably mounted to the extension member and slideably engages the inner wall of the housing cavity. Since the sleeve is in slideable relationship with the extension member, axial displacement of the extension member relative to the sleeve may occur after the sleeve is precluded from further distal axial displacement by engagement of the sleeve with a distal shoulder barrier formed at the distal opening of the housing. The outer struts integrally and confluently interconnect to form a self-hinged central joint which is axially displaceable distally relative to the sleeve during the lateral collapse of the outer struts. A pair of laterally and oppositely spaced expander struts are integrally joined respectively to each of the outer struts to form first self-hinged joints about which the distal ends of the expander struts may pivot to assist in the opening and closing of the outer struts. The proximate ends of the expander struts are fixed to the distal end of the extension member to form second self-hinged joints about which the proximate ends of the expander struts may pivot as the outer struts open or close. As the extension member is withdrawn into the housing cavity the expander struts will begin to laterally collapse which induces collapse of of the outer struts as the support truss is withdrawn into the cavity. Likewise, when the extension member is advanced axially in a distal direction a sufficient distance, the collapsed truss will extend distally from the distal end of the housing while the sleeve is precluded by the distal shoulder barrier from advancing axially; the continued axial advance of the extension member after the sleeve has been precluded from further axial movement will cause the expander struts to pivot about the first and second hinged joints and open the outer struts thereby forming a truss support platform.

Thus, a lower sterilization risk retractor of inexpensive construction is presented which permits the surgeon to dispose of the retractor after a single use.

BRIEF DESCRIPTION OF THE DRAWINGS

These and other features and advantages will become appreciated as the same become better understood with reference to the following specification, claims and drawings wherein:

FIG. 1 is a perspective view of the disposable endoscopic retractor instrument of this invention.

FIG. 2 is a part cross-sectional view of FIG. 1 illustrating the retractor in a fully opened position.

FIG. 3 is a part cross-sectional left side elevational view of FIG. 2.

FIG. 4 is a part cross-sectional view of FIG. 2 illustrating the collapsibility of the support truss of the retractor instrument.

FIG. 5 is a part cross-sectional view of FIG. 4 illustrating the support truss in a collapsed state during withdrawal of the support truss into the instrument housing.

FIG. 6 is a part cross-sectional view of FIG. 1 illustrating the support truss in a partially withdrawn configuration.

FIG. 7 is a part cross-sectional view of FIG. 6 illustrating the support truss completely withdrawn into the instrument housing.

FIG. 8 is a cross-sectional view of FIG. 5 taken along the line 8—8 illustrating another embodiment of the sleeve member of this invention.

DETAILED DESCRIPTION

Referring to FIG. 1, a disposable retractor instrument 1 is shown in perspective with the truss support platform 2 fully extended from the distal end of the housing 3. As can be seen in FIG. 1, truss support platform 2 has a self-hinging central joint 4, a longitudinal axis 5, and first laterally spaced self-hinging joints 6 and 6'; self-hinging central joint 4 and first laterally spaced self-hinging joints 6 and 6' are integrally formed in lateral outer struts 7 and 7' defining a continuous distal closure bridge 8 or confluence between lateral outer struts 7 and 7'. As can be seen from FIG. 1, self-hinging central joint 4 and first laterally spaced self-hinging joints 6 and 6' permit outer struts 7 and 7' to be laterally collapsable; the lateral collapsability of lateral outer struts 7 and 7' can be more readily described by referenced to FIG. 2. As can be seen in FIG. 2, the proximate ends 9 and 9' of the outer struts are oppositely and laterally spaced from the longitudinal axis 5 of the retractor instrument. The distal ends of outer struts 7 and 7' are integrally connected to sleeve member 10 which has an axial bore therethrough 11 to permit the extension and retraction of extension member 12 relative to housing 3 during the opening and closing, respectively, of the truss support platform 2 when extension member 12 is extended from the housing and when it is retracted within the housing. FIG. 2 further illustrates outer strut members 7 and 7' adjacent the distal end of sleeve 10 having second laterally spaced self-hinged joints 13 and 13' which permit articulation of outer struts 7 and 7' relative to sleeve member 10 laterally during the lateral collapse or expansion of truss support platform 2.

The structure of truss support platform 2, as further illustrated in FIG. 2, includes a pair of expander struts 14 and 14' which are oppositely and laterally spaced from longitudinal axis 5 and have distal ends which are integrally formed with outer struts 7 and 7' to form first expander joints 15 and 15' which are self-hinging and permit articulation of expander struts 14 and 14' relative to outer struts 7 and 7'. The proximate ends 16 and 16' of expander struts 14 and 14' respectively are structurally integral with the distal tip of extension member 12. As can be further seen in FIG. 2, second expander joints 17 and 17' are self-hinging and are laterally and oppositely spaced from the longitudinal axis to permit articulation of expander struts 14 and 14' relative to the extension member 12.

Further definition of the structure of disposable retractor instrument 1 is illustrated in FIG. 3 wherein it can be seen that the sleeve 10 is at its distal limit of travel axially within housing cavity 18. Housing orifice 19 located at the distal end of housing 18 has a diameter which is less than the internal diameter of the housing thereby forming a shoulder barrier 20 which precludes further axial movement in a distal direction of the sleeve 10. Extension member 12 is slideably mounted within housing 3 by bushing 21 which is mounted in fixed relationship to extension member 12 thereby permitting relative axial movement between extension member 12 and the housing. Axial movement of extension member 12 is initiated by either pushing or pulling thrust cap 22 which is threaded to the proximate end of the extension member. A set screw 23 is utilized to lock extension member 12 into fixed relationship with the housing.

FIG. 4 illustrates the lateral collapse of the truss support platform 2 upon retraction of the extension member 12 into the housing. As can be seen in FIG. 4, upon sufficient movement of extension member 12 proximally, shoulder barrier 20 bears against lateral walls 24 and 24' of outer struts 7 and 7' as the sleeve 10 is retracted into the housing. First expander joints 15 and 15' as extension member 12 is retracted into the housing permit articulation of expander struts 14 and 14' relative to the outer struts 7 and 7'; second expander joints 17 and 17' permit articulation of expander struts 14 and 14' relative to extension member 12 such that upon retraction of extension member 12 into the housing expander struts 14 and 14' laterally collapse toward each other while the outer struts 7 and 7' collapse laterally. FIG. 6 illustrates truss support platform 2 fully collapsed laterally and partially withdrawn into housing cavity 18 and FIG. 7 illustrates the truss support platform fully retracted into the housing. Both FIGS. 6 and 7 illustrate the axial displacement of sleeve member 10 during retraction of the truss support platform into the housing.

The truss support platform, sleeve member and extension member form one continuous plastic member which may be molded in a single operation thereby substantially reducing the cost of manufacture of the retractor instrument. In another embodiment illustrated in FIG. 8 the sleeve member may be molded in hemispherical or arcuate sections which integrally connect with outer struts 25 and 25' respectively and are held in slideable relationship with extension member 12 by the inner wall of the housing which also prevents the sleeve hemispherical sections from separating while clamped to the extension member.

To utilize the disposable retractor instrument, the truss support platform is first retracted into the housing 3 sufficiently to permit the housing to be transported through a trocar which is in communication with the operative region of the patient. To expand the truss support platform after the distal portion of the housing 3 has been transported to the operative region, an external force is applied to the thrust cap 22 which forces the extension member 12 to displace axially while at the same time the sleeve is axially displaced in the direction of the shoulder barrier 20. When sleeve 10 is precluded from further axial movement by shoulder barrier 20 the extension member 12 continues to move axially and expander struts 14 and 14' will articulate both about second expander joints 17 and 17' and first expansion joints 15 and 15' to open the truss platform. The open truss platform presents a sufficient engagement surface to bear against an internal organ and retract it a sufficient distance within the operative region to render the operative area accessible to the surgeon.

Although the retractor instrument of this invention is in its preferred embodiment shown to be made of a plastic material, other materials having the elastic properties of plastic may also be used in the construction of the device of this invention.

While a disposable retractor device has been shown and described, it is to be understood that it is subject to many modifications without departing from the scope and spirit of the claims as recited herein.

We claim:

1. An endoscopic surgical retractor instrument for supporting internal organs comprising:
   a) a housing having an inner and outer surface, a longitudinal axis, and a proximate and distal end, said housing having a first opening at said distal end and a second opening at said proximate end and an axially extending cavity bounded by said inner surface where said cavity communicates with said first and second openings forming a passageway through said housing;
   b) an extension member slideably carried by said housing and extending at least in part in said cavity for axial displacement relative to said housing such that said extension member may upon sufficient distal axial displacement relative to said housing extend in part distally from said distal end of said housing and upon sufficient proximate axial displacement said extension member may be retracted proximately of said distal end of said housing;
   c) a sleeve having an axially extending conduit forming a passageway therethrough for receiving said extension member where said sleeve is so mounted in concentric relationship to said extension member to permit slideable extensible axial displacement of said extension member relative to said sleeve and a distal barrier extending from said housing in a radial direction adjacent said distal end of said housing and defining a limit to the distal axial displacement of said sleeve such that upon engagement of said sleeve with said barrier said extension member is distally extensible relative to said sleeve; and
   d) a laterally collapsible and expandable self-hinging truss platform so carried by said sleeve and said extension member such that upon axial extension of said extension member sufficiently distal of said distal end of said housing said self-hinging support platform may be opened and upon sufficient retraction of said extension member proximally within said housing said self-hinging truss support platform may be laterally collapsed.

2. The surgical retractor instrument recited in claim 1 wherein said self-hinging truss support platform comprises a pair of lateral outer struts integrally connected to said sleeve, a distal closure bridge integrally interconnecting said outer struts to form first laterally spaced self-hinging joints, and a pair of expander struts having first and second ends respectively where each said expander strut is integrally connected at said first end to said extension member and distally extending from said extension member, and where each said second end respectively of said expander struts is integrally connected respectively to one of said outer struts.

3. The surgical retractor instrument recited in claim 2 wherein said distal closure bridge contains a self-hinging central joint intermediate said outer struts such that said distal closure bridge may laterally collapse upon the lateral collapse of said outer struts and laterally expand upon the lateral expansion of said outer struts.

4. The surgical retractor instrument recited in claim 3 wherein each said second end of said expander struts respectively forms a first self-hinging expander joint with one of said outer struts and each said first end of said expander struts respectively forms a second self-hinging expander joint with said extension member.

5. The surgical retractor instrument recited in claim 1 wherein said truss support platform, said extension member, and said sleeve are made of a plastic material.

6. The surgical retractor instrument recited in claim 1 wherein said sleeve comprises a first arcuate section slideably carried by said extension member and a second arcuate section slideably carried by said extension member where said first and second arcuate sections are captively contained within said housing and radially and oppositely spaced therein.

7. The surgical retractor instrument recited in claim 6 wherein said self-hinging truss support platform comprises a pair of lateral outer struts integrally connected to said sleeve, a distal closure bridge integrally interconnecting said outer struts to form first laterally spaced self-hinging joints, and a pair of expander struts having first and second ends respectively where each said expander strut is integrally connected at said first end to said extension member and distally extending from said extension member, and where each said second end respectively of said expander struts is integrally connected respectively to one of said outer struts.

8. The surgical retractor instrument recited in claim 7 wherein said distal closure bridge contains a self-hinging central joint intermediate said outer struts such that said distal closure bridge may laterally collapse upon the lateral collapse of said outer struts and laterally expand upon the lateral expansion of said outer struts.

9. The surgical retractor instrument recited in claim 8 wherein each said second end of said expander struts respectively forms a first self-hinging expander joint with one of said outer struts and each said first end of said expander struts respectively forms a second self-hinging expander joint with said extension member.

10. The surgical retractor instrument recited in claim 7 wherein said pair of lateral outer struts are integrally connected respectively to said first and second arcuate sections.

11. An endoscopic surgical retractor instrument for supporting internal organs comprising:
   a) a housing having an inner and outer surface, a longitudinal axis, and a proximate and distal end, said housing having a first opening at said distal end and a second opening at said proximate end and an axially extending cavity bounded by said inner surface where said cavity communicates with said first and second openings forming a passageway through said housing;
   b) an extension member slideably carried by said housing and extending at least in part in said cavity for axial displacement relative to said housing such that said extension member may upon sufficient distal axial displacement relative to said housing extend in part distally from said distal end of said housing and upon sufficient proximate axial displacement said extension member may be retracted proximately of said distal end of said housing;
   c) a sleeve having an axially extending conduit forming a passageway therethrough for receiving said extension member where said sleeve is so mounted in concentric relationship to said extension member to permit slideably extensible axial displacement of said extension member relative to said sleeve and a distal barrier extending from said housing in a radical direction adjacent said distal end of said housing and defining a limit to the distal axial displacement of said sleeve such that upon engagement of said sleeve with said barrier said extension member is distally extensible relative to said sleeve; and d) a laterally collapsible and expandable self-hinging truss platform so carried by said sleeve and said extension member such that upon axial extension of said extension member sufficiently distal of said distal end of said housing said self-hinging support platform may be opened and upon sufficient retraction of said extension member proximally within said housing said self-hinging truss support platform may be laterally collapsed wherein said self-hinging truss support platform comprises a pair of lateral outer struts integrally connected to said sleeve, a distal closure bridge integrally interconnecting said outer struts to form first laterally spaced self-hinging joints, and a pair of expander struts having first and second ends respectively where each said expander strut is integrally connected at said first end to said extension member and distally extending from said extension member, and where each said second end respectively of said expander struts is integrally connected respectively to one of said outer struts.

12. The surgical retractor instrument recited in claim 11 wherein said distal closure bridge contains a self-hinging central joint intermediate said outer struts such that said distal closure bridge may laterally collapse upon the lateral collapse of said outer struts and laterally expand upon the lateral expansion of said outer struts.

13. The surgical retractor instrument recited in claim 12 wherein each said second end of said expander struts respectively forms a first self-hinging expander joint with one of said outer struts and each said first end of said expander struts respectively forms a second self-hinging expander joint with said extension member.

14. The surgical retractor instrument recited in claim 11 wherein said sleeve comprises a first arcuate section slideably carried by said extension member and a second arcuate section slideably carried by said extension member where said first and second arcuate sections are captively contained within said housing and radially and oppositely spaced therein.

15. The surgical retractor instrument recited in claim 14 wherein said self-hinging truss support platform comprises a pair of lateral outer struts integrally connected to said sleeve, a distal closure bridge integrally interconnecting said outer struts to form first laterally spaced self-hinging joints, and a pair of expander struts having first and second ends respectively where each said expander strut is integrally connected at said first end to said extension member and distally extending from said extension member, and where each said second end respectively of said expander struts is integrally connected respectively to one of said outer struts.

16. The surgical retractor instrument recited in claim 15 wherein said distal closure bridge contains a self-hinging central joint intermediate said outer struts such that said distal closure bridge may laterally collapse upon the lateral collapse of said outer struts and laterally expand upon the lateral expansion of said outer struts.

17. The surgical retractor instrument recited in claim 16 wherein each said second end of said expander struts respectively forms a first self-hinging expander joint with one of said outer struts and each said first end of said expander struts respectively forms a second self-hinging expander joint with said extension member.

* * * * *